US 6,702,789 B1

United States Patent
Owens et al.

(10) Patent No.: US 6,702,789 B1
(45) Date of Patent: Mar. 9, 2004

(54) CATHETER HAVING INSERTION CONTROL MECHANISM AND ANTI-BUNCHING MECHANISM

(75) Inventors: Warren D. Owens, Salt Lake City, UT (US); William R. Hawes, North Salt Lake City, UT (US); Cary P. Jenkins, Powell, OH (US); Ken D. Hargett, Pearland, TX (US)

(73) Assignee: Alcove Medical, Inc., Salt Lake City, UT (US)

( * ) Notice: Subject to any disclaimer, the term of this patent is extended or adjusted under 35 U.S.C. 154(b) by 357 days.

(21) Appl. No.: 09/610,644

(22) Filed: Jun. 12, 2000

Related U.S. Application Data

(63) Continuation of application No. 09/038,465, filed on Mar. 11, 1998, now abandoned.
(60) Provisional application No. 60/040,678, filed on Mar. 11, 1997.

(51) Int. Cl.⁷ .......................... A61M 1/00; A61M 5/00; A61M 25/00; A62B 9/02
(52) U.S. Cl. .................. 604/264; 604/27; 604/528; 128/207.14; 128/200.16
(58) Field of Search .............................. 604/23, 24, 26, 604/27, 28, 29, 508, 513, 514, 119, 163, 171, 35, 101.01–101.05, 103, 43, 45, 103.01–103.09, 523, 528; 128/207.15, 207.16, 207.14, 912, 200.26, DIG. 12

(56) References Cited

U.S. PATENT DOCUMENTS

| | | | | |
|---|---|---|---|---|
| 3,991,762 A | * | 11/1976 | Radford | 128/200.26 |
| 4,327,723 A | | 5/1982 | Frankhouser | |
| 4,825,859 A | | 5/1989 | Lambert | |
| 4,838,255 A | | 6/1989 | Lambert | |
| 4,967,743 A | | 11/1990 | Lambert | |
| 5,060,646 A | | 10/1991 | Page | |
| 5,107,829 A | | 4/1992 | Lambert | |
| 5,133,345 A | * | 7/1992 | Lambert | 128/202.16 |
| 5,139,018 A | * | 8/1992 | Brodsky et al. | 128/207.14 |
| 5,238,218 A | | 8/1993 | Mackal | |
| 5,277,177 A | | 1/1994 | Page et al. | |
| 5,466,230 A | | 11/1995 | Davila | |
| 5,642,726 A | | 7/1997 | Owens et al. | |

* cited by examiner

Primary Examiner—Brian L. Casler
Assistant Examiner—Matthew DeSanton
(74) Attorney, Agent, or Firm—Bell, Boyd & Lloyd, LLC

(57) ABSTRACT

The present invention is a catheter having a tube and including mechanisms that provide precision control over insertion and retraction of the catheter tube. The catheter is particularly adapted for introduction into the pulmonary system. The catheter includes an insertion depth control mechanism that acts as a stop and provides a tactile indication to the person inserting the catheter tube that a predetermined position has been reached. The catheter also includes an anti-bunching mechanism to prevent bunching of a protective sleeve disposed around the catheter tube, thereby reducing interference from the sleeve during insertion of the catheter tube.

3 Claims, 4 Drawing Sheets

CATHETER HAVING INSERTION CONTROL MECHANISM AND ANTI-BUNCHING MECHANISM

CROSS REFERENCE TO RELATED APPLICATION

This application is a continuation of Ser. No. 09/038,465, filed Mar. 11, 1998 now abandoned, which claims priority to provisional application Ser. No. 60/040,678, filed Mar. 11, 1997.

TECHNICAL FIELD

The present invention relates to medical catheters, and more particularly to catheters used to remove substances from, or introduce substances into, the pulmonary system or gastrointestinal tract of a patient.

BACKGROUND OF THE INVENTION

In certain medical treatment situations, catheters must be precisely introduced into a patient's pulmonary system or gastrointestinal tract for various functions. For example, a patient may require involuntary aspiration of secretions from the patient's lungs. In this situation, a suction catheter can be introduced into the patient's airway and lungs to remove the secretions via suction through the catheter. In addition, a patient may require introduction of various substances into the body through such catheters. For example, a patient may require the introduction of a lavage solution into the lungs to loosen secretions without interfering with ventilation.

Respiratory distress frequently occurs in infants and small children, especially prematurely born infants. Premature infants may require repeated pulmonary intervention. When an infant or small child is unable to effectively breathe on their own, intubation and involuntary ventilation is provided via an endotracheal tube. In caring for infant patients, it is necessary to periodically suction out secretions that would otherwise accumulate in the infant's lungs. This requires periodic involuntary removal of secretions from the lungs via a small suction catheter tube without injury to the lungs. Suctioning and/or introduction of therapeutic substances may take place intermittently during ventilation.

Suctioning is generally accomplished by introducing and advancing one end of a flexible suction catheter tube into the endotracheal tube and applying suction to the other end of the catheter tube. To reduce the extent of airway occlusion, the catheter tube is typically withdrawn from the endotracheal tube when the catheter is not in use.

Before the catheter tube is advanced through the endotracheal tube, the catheter tube may be "exposed" within the catheter assembly. However, many catheters include a flexible sleeve that covers the span of tubing between the fittings of a catheter to avoid the introduction of microbial pathogens during intubation. The sleeve encloses the catheter tube and preserves the sterility of the tube in a closed system. The sleeve remains fixed to the fittings of the catheter. The sleeve is flexible so that the catheter can be advanced by manipulating the catheter from the outside of the sleeve. Thus, the catheter may be intermittently introduced without breaking the sterile field created by the sleeve around the catheter.

Precise control over the placement of the catheter tube is also required to reduce the risk of injury during placement. The catheter must be advanced far enough to effectively reach the lungs without damaging tissue by overextension of the catheter. The use of a catheter having a protective sleeve further impacts control over the catheter during placement. As the catheter is fully advanced, the sleeve may bunch, making precise control more difficult. Thus, there is a need for a catheter having a mechanism for controlling insertion depth while preventing bunching of the protective sleeve as the catheter is inserted.

SUMMARY OF THE INVENTION

The present invention is a catheter having a tube and including mechanisms that provide precision control over insertion and retraction of the catheter tube. The catheter is particularly adapted for introduction into the pulmonary system. The catheter includes an insertion depth control mechanism that acts as a stop and provides a tactile indication to the person inserting the catheter tube that a predetermined position has been reached. The catheter also includes an anti-bunching mechanism to prevent bunching of a protective sleeve disposed around the catheter tube, thereby reducing interference from the sleeve during insertion of the catheter tube.

In one embodiment, the insertion depth control mechanism comprises an insertion control member that is adjustable positioned on the catheter tube. The insertion control member includes a releasably catch to permit adjustment of its position along the catheter tube. When placed in a predetermined position that corresponds to a predetermined insertion depth, the insertion control member acts as a stop against a connector or other form attached to the tube. When the insertion control member reaches the connector or form during insertion of the tube, it bumps against the connector or form and stops the advancement of the catheter tube at a predetermined length. This resistance provides a tactile response, or feel, to a person inserting the catheter, which indicates that the catheter tube has been inserted to the predetermined depth. The insertion control member can comprise a number of different shape.

In one embodiment, the anti-bunching mechanism comprises a sleeve spreader including an outer surface concentrically disposed around the catheter tube and adjacent a tube opening of a distal connector attached to the catheter. The sleeve spreader deflects the sleeve away from the tube opening of the distal connector and prevents it from bunching at the tube opening, thereby avoiding interference with advancement of the catheter tube.

DETAILED DESCRIPTION OF THE PREFERRED EMBODIMENTS

While the present invention will be described fully hereinafter with reference to the accompanying drawings, in which a particular embodiment is shown, it is to be understood at the outset that persons skilled in the art may modify the invention herein described while still achieving the desired result of this invention. Accordingly, the description which follows is to be understood as a broad informative disclosure directed to persons skilled in the appropriate arts and not as limitations of the present invention.

Figure 1:
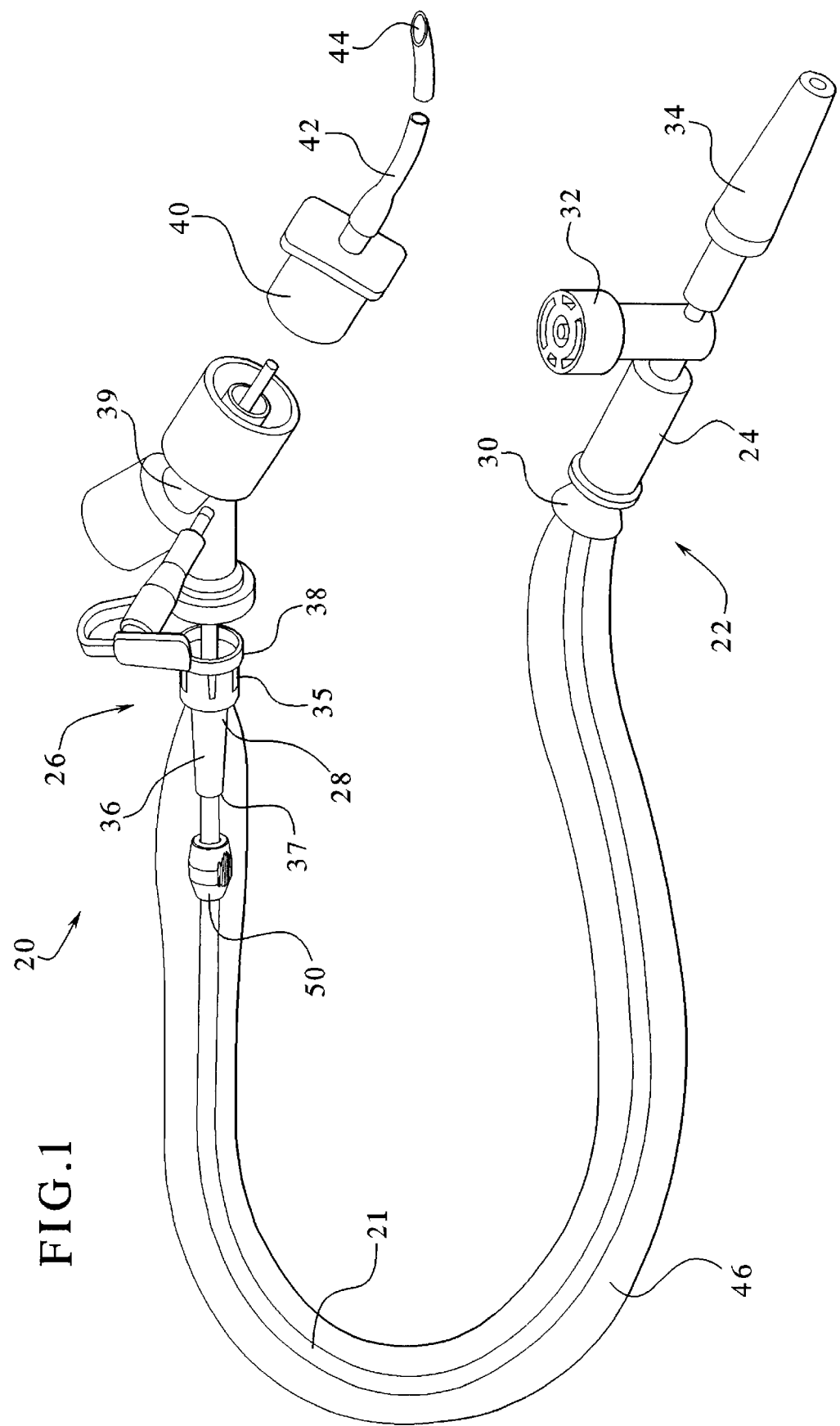
FIG. 1 is a perspective view of a catheter of the present invention including a connector for a ventilation apparatus.

FIG. 1 is an exploded view of a suction catheter 20 and associated attachments for use in a typical ventilator circuit. The suction catheter 20 incorporates an insertion depth control mechanism and an anti-bunching mechanism as described herein. The suction catheter 20 includes a catheter tube 21, aproximal end 22 having a proximal connector assembly 24, and a distal end 26 having a distal spreader connector 28. The proximal connector assembly 24 includes a sleeve collar 30, a vacuum valve 32, and a terminal connector 34. The distal spreader connector 28 includes a sleeve collar 35 and a generally cone-shaped extension 36 that extends toward the proximal end 22 of the catheter 20. The cone-shaped extension includes a tube aperture 37. The catheter tube 21 passes through the tube aperture 37. The distal spreader connector 28 has a fitting 38 that can be connected to an adapter device 39. To complete the ventilation circuit, the adapter device 39 is connected to a conventional ventilation adapter 40 that includes an endotracheal tube 42 having an end opening 44. Other components may be used in connection with the suction catheter 20 without departing from the present invention, such as those disclosed in U.S. Pat. No. 5,642,726, which is incorporated herein by reference.

The catheter tube 21 of the suction catheter 20 is surrounded by a flexible external sleeve 46 that spans from the proximal connector assembly 24 to the distal spreader connector 28, as shown in FIG. 1. The external sleeve 46 is attached to the proximal connector assembly 24 within the sleeve collar 30 and the distal spreader connector 28 within the sleeve collar 35. The sleeve 46 may be banded to the sleeve collars 30 and 35 or adhered thereto. The external sleeve 46 encloses the catheter tube 21 to preserve its sterility during use in a closed system.

During intubation, the catheter tube 21 of the suction catheter 20 is introduced into the endotracheal tube 42 through the distal spreader connector 28 and the adapter device 39 and advanced to a predetermined depth. The depth of insertion is controlled by an insertion control member 50. During insertion of the catheter tube 21, the insertion control member 50 acts as a stop against the cone-shaped extension 36 of the distal spreader connector 28, thus stopping the advancement of the catheter at a predetermined depth. The insertion control member 50 also provides a tactile feel to the operator when it bumps against the extension 36, thereby signaling to the operator that the proper depth has been reached.

Figure 2A:
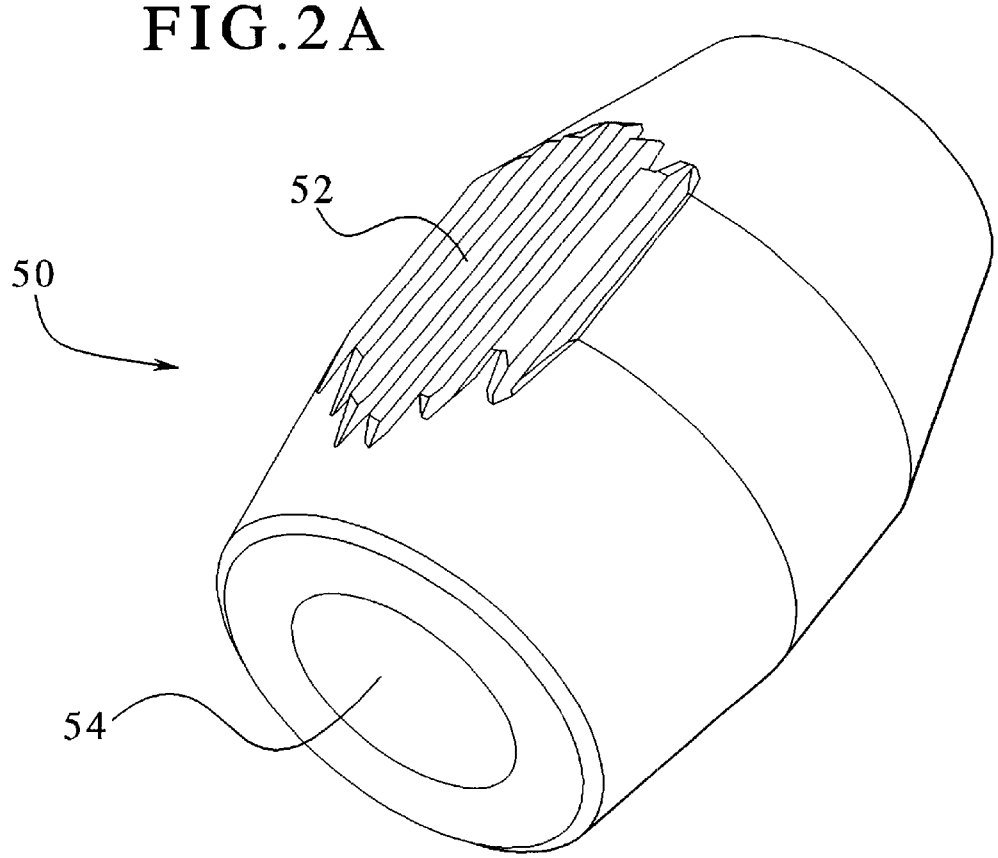
FIG. 2A is a perspective view of a first embodiment of an insertion control member of the present invention.
Figure 2B:
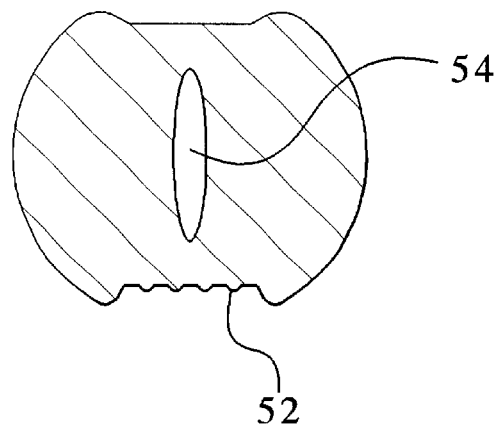
FIG. 2B is a cross-sectional view of the insertion control member shown in FIG. 2A taken transversely through the center of the insertion control member.

In the embodiment depicted in FIG. 1, the insertion control member 50 has a generally barreled shape as shown in FIGS. 2A and 2B. The insertion control member 50 includes two flattened grip portions 52 and a tube passage 54. As shown in FIG. 2B, the tube passage 54 has an elongated cross-section near the center of the insertion control member 50. The catheter tube 21 passes through the tube passage 54 and the elongated configuration of the tube passage 54 grips the catheter tube 21 to hold the insertion control member 50 at a predetermined position along the catheter tube 21. The catheter tube 21 may include indicia to help facilitate depth adjustment of the catheter tube 21 via the insertion control member 50. The position of the insertion control member 50 can be adjusted by an operator pinching the insertion control member 50 at the flattened grip portions 52 to flex the elongated cross-section of the of the tube passage 54 to form a relatively wider cross-section. The wider cross-section allows the operator to slide the insertion control member 50 to a new position on the catheter tube 21. When the insertion control member 50 is repositioned, the operator releases the flattened grip portions 52 so that the cross-section of the tube passage 54 returns to its elongated configuration. Alternatively, the cross-section of the tube passage 54 may include other features to help grip the catheter tube 21, such as teeth or other projections.

Figure 3:
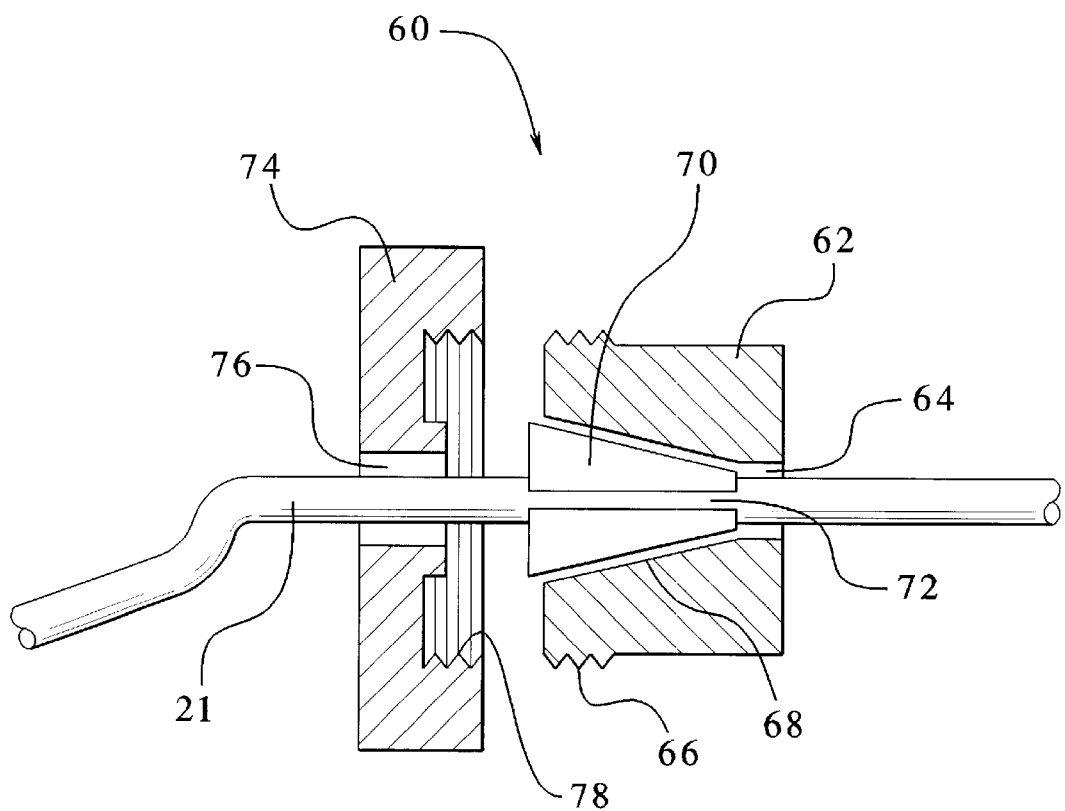
FIG. 3 is a cross-sectional side view of a second embodiment of an insertion control member of the present invention.

FIG. 3 shows an alternate embodiment in the form of an insertion control assembly 60. The insertion control assembly 60 includes a threaded sleeve 62 having a thru-hole 64 and external threads 66 on one end of the sleeve 62. The thru-hole 64 has a tapered surface 68 that accepts a tapered collet 70, as shown in FIG. 3. The tapered collet 70 includes a channel 72 therethrough. A mating nut 74 includes a thru-hole 76 and internal threads 78 that are adapted to engage the external threads 66 of the threaded sleeve 62. The catheter tube 21 passes through the thru-hole 64 of the threaded sleeve 62, the channel 72 of the tapered collet 70, and the thru-hole 76 of the mating nut 74. When the threaded sleeve 62 and the mating nut 74 are engaged and tightened, the threaded sleeve 62 deflects and compresses the tapered collet 70 around the catheter tube 21, thereby securing the insertion control assembly 60 to the catheter tube 21.

Figure 4:
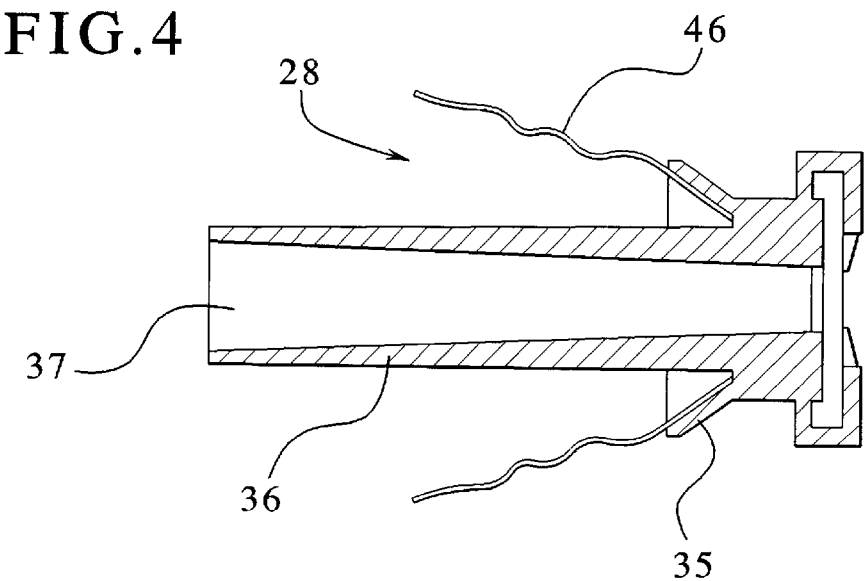
FIG. 4 is a cross-sectional view of a sleeve spreader of the catheter shown in FIG. 1.

FIG. 4 is a cross-sectional view of the distal spreader connector 28 shown in FIG. 1. As the catheter tube 21 is advanced through the distal spreader connector 28 and the adapter device 38, the external sleeve 46 begins to bunch up near the distal spreader connector 28. The cone-shaped extension 36 of the distal spreader connector 28 acts to spread or deflect the sleeve 46 as the catheter tube 21 is advanced and prevent the sleeve 46 from interfering with the tube opening or aperture 37 of the extension 36 of the distal spreader connector 28. The sleeve 46 is attached to the distal spreader connector 28 between the collar 35 and the extension 36, as shown in FIG. 4.

Figure 5A:
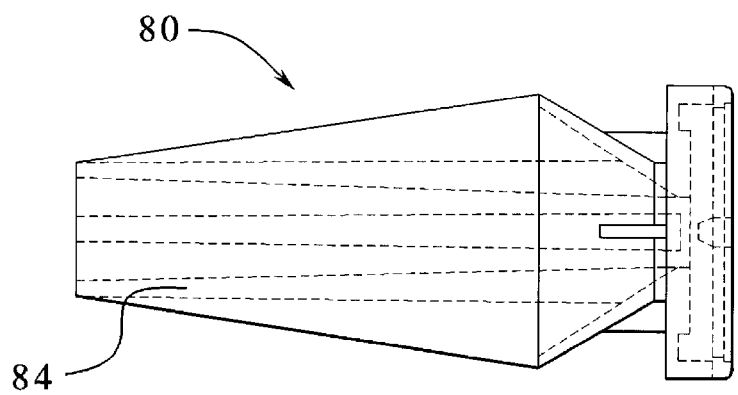
FIG. 5A is an elevational view of a second embodiment of a sleeve spreader of the present invention.
Figure 5B:
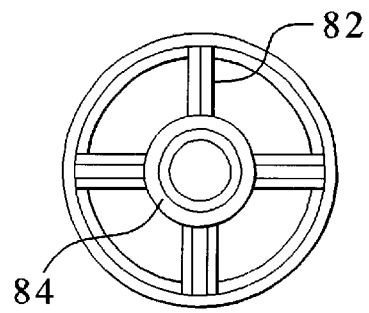
FIG. 5B is a cross-sectional view of the sleeve spreader shown in FIG. 5A.

FIGS. 5A and 5B show an alternate embodiment in the form of a distal spreader connector 80. In this embodiment, the distal spreader connector 80 includes a set of four tapered ribs 82 that extend from an extension 84. The tapered ribs 82 provide further deflection and spreading of the sleeve 46 as the catheter tube 21 is advanced. Accordingly, the distal spreader connector 80 deflects the sleeve adjacent to the tube opening of the distal catheter connector.

While the specific embodiments have been illustrated and described, numerous modifications come to mind without significantly departing from the spirit of the invention and the scope of protection is only limited by the scope of the accompanying Claims.

What is claimed is:

1. A catheter for use with an aspirating apparatus including an indwelling endotracheal tube having a proximal end connector, the catheter comprising:

a catheter tube adapted to be selectively advanced through the proximal end connector and the endotracheal tube into a respiratory system of a patient to a predetermined depth;

a distal catheter connector connected to the proximal end connector of the endotracheal tube, the distal catheter connector including a tube opening that allows the catheter tube to pass therethrough and into the endotracheal tube;

a flexible sleeve connected to the distal catheter connector and disposed around the catheter tube;

means for stopping the advancement of the catheter tube at the predetermined depth wherein said stopping means is disposed within the flexible sleeve; and means for deflecting the flexible sleeve adjacent to the tube opening of the distal catheter connector wherein a portion of said deflecting means is disposed within the flexible sleeve.

2. The catheter of claim 1, wherein the means for stopping is adjustable.

3. The catheter of claim 2, wherein the tube includes indicia of length printed thereon to aid an operator in adjusting the means for stopping to the predetermined length.

* * * * *